US008754126B2

(12) United States Patent
Lai et al.

(10) Patent No.: US 8,754,126 B2
(45) Date of Patent: Jun. 17, 2014

(54) METHODS FOR IMPROVING TOLERANCE, DIGESTION, AND LIPID SOLUBLE NUTRIENT ABSORPTION IN AN INFANT, TODDLER, OR CHILD

(75) Inventors: Chron-Si Lai, Blacklick, OH (US); Keith A. Garleb, Pickerington, OH (US); John B. Lasekan, Columbus, OH (US); Steven R. Davis, Columbus, OH (US); Christopher T. Cordle, Centerburg, OH (US); Russell J. Merritt, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/333,943

(22) Filed: Dec. 21, 2011

(65) Prior Publication Data

US 2012/0172434 A1 Jul. 5, 2012

Related U.S. Application Data

(60) Provisional application No. 61/428,168, filed on Dec. 29, 2010, provisional application No. 61/428,173, filed on Dec. 29, 2010, provisional application No. 61/428,176, filed on Dec. 29, 2010, provisional application No. 61/428,177, filed on Dec. 29, 2010, provisional application No. 61/428,185, filed on Dec. 29, 2010.

(51) Int. Cl.
*A61K 31/20* (2006.01)
*A23D 7/00* (2006.01)
*A23L 1/29* (2006.01)
*A23L 1/30* (2006.01)

(52) U.S. Cl.
CPC .................................... *A23L 1/296* (2013.01); *A23L 1/3008* (2013.01)
USPC ........... 514/558; 514/557; 426/601; 426/611; 426/612

(58) Field of Classification Search
CPC ............................. A23L 1/296; A23L 1/3008
USPC ............ 42/531, 601, 611, 612; 513/553, 557, 513/558
See application file for complete search history.

(56) References Cited

U.S. PATENT DOCUMENTS

| | | | |
|---|---|---|---|
| 2,236,517 A | 4/1941 | Harris | |
| 3,253,992 A | 5/1966 | Brooks | |
| 3,542,560 A | 11/1970 | Tomarelli et al. | |
| 3,841,833 A | 10/1974 | Minkema et al. | |
| 4,310,561 A | 1/1982 | Buddemeyer et al. | |
| 5,045,337 A | 9/1991 | El-Nokaly et al. | |
| 5,179,122 A | 1/1993 | Greene et al. | |
| 5,248,509 A | 9/1993 | Bruin | |
| 5,308,832 A * | 5/1994 | Garleb et al. | 514/5.5 |
| 5,434,182 A | 7/1995 | Isaacs et al. | |
| 5,660,842 A | 8/1997 | Petschow | |
| 6,013,665 A | 1/2000 | DeMichele et al. | |
| 6,077,558 A | 6/2000 | Euber | |
| 6,248,784 B1 | 6/2001 | Kuchan et al. | |
| 6,306,908 B1 | 10/2001 | Carlson et al. | |
| 6,365,218 B1 | 4/2002 | Borschel | |
| 6,406,729 B1 | 6/2002 | Miller et al. | |
| 6,426,078 B1 | 7/2002 | Bauer et al. | |
| 6,485,716 B1 | 11/2002 | Fei et al. | |
| 6,503,545 B1 | 1/2003 | Perlman et al. | |
| 6,569,478 B1 | 5/2003 | Leser et al. | |
| 6,576,667 B2 | 6/2003 | Strohmaier et al. | |
| 6,608,222 B2 | 8/2003 | Bonsignore et al. | |
| 7,182,950 B2 | 2/2007 | Garti et al. | |
| 7,402,327 B2 | 7/2008 | Zhong et al. | |
| 7,494,680 B2 * | 2/2009 | Moriwaki et al. | 426/601 |
| 7,595,079 B2 | 9/2009 | Lall et al. | |
| 8,076,497 B2 | 12/2011 | Lai et al. | |
| 2002/0176911 A1 | 11/2002 | Borschel et al. | |
| 2003/0054082 A1 | 3/2003 | Koike et al. | |
| 2003/0096035 A1 | 5/2003 | Perlman et al. | |
| 2004/0022926 A1 | 2/2004 | Bartocci et al. | |
| 2004/0209953 A1 | 10/2004 | Wai Lee | |
| 2004/0213853 A1 | 10/2004 | Byard et al. | |
| 2005/0013848 A1 | 1/2005 | Moriwaki et al. | |
| 2005/0031736 A1 | 2/2005 | Nguyen et al. | |
| 2005/0032892 A1 | 2/2005 | Kelm et al. | |
| 2005/0106216 A1 | 5/2005 | Maurer et al. | |
| 2005/0214413 A1 | 9/2005 | McAnalley et al. | |
| 2006/0034934 A1 | 2/2006 | DeGuise et al. | |
| 2007/0141124 A1 | 6/2007 | Johns et al. | |

(Continued)

FOREIGN PATENT DOCUMENTS

| | | |
|---|---|---|
| EP | 1925294 | 5/2008 |
| EP | 2062570 | 5/2009 |

(Continued)

OTHER PUBLICATIONS

Wikipedia article, "Palmitate", last accessed Jan. 31, 2012.
Wikipedia article, "Triglyceride", last accessed Jan. 31, 2012.
Wikipedia article, "Fat triglyceride shorthand formula", last accessed Jan. 31, 2012.
Schanler, Human Milk Poster Symposium, "Fatty Acid Soaps May Be Responsible for Poor Fat Absorption in Premature Infants Fed Fortified Human Milk (FHM)," Pediatric Research, vol. 45, p. 290A (1999).
Little, et al., "Dose-related Effects of Lauric Acid on Antropyloroduodenal Motility, Gastrointestinal Hormone Release, Appetite, and Energy Intake in Healthy Men," Am. J. Physiol. Regul. Integr. Comp. Physiol., vol. 289, pp. R1090-R1098 (2005).

(Continued)

*Primary Examiner* — My-Chau T Tran
(74) *Attorney, Agent, or Firm* — Calfee, Halter & Griswold LLP (57) ABSTRACT

Disclosed are nutritional formulations including predigested fats that can be administered to preterm infants, infants, toddlers, and children for improving tolerance, digestion, and absorption of nutrients and for reducing the incidence of necrotizing enterocolitis, colic, and short bowel syndrome. The predigested fats include fatty acid-containing monoglycerides and/or a fatty acid component.

19 Claims, 2 Drawing Sheets

(56) References Cited

U.S. PATENT DOCUMENTS

| | | |
|---|---|---|
| 2008/0058415 A1 | 3/2008 | Shulman et al. |
| 2008/0089981 A1 | 4/2008 | Butler et al. |
| 2009/0220638 A1 | 9/2009 | Pablos Perez |
| 2009/0298937 A1 | 12/2009 | Petschow |
| 2010/0256403 A1 | 10/2010 | Lai et al. |
| 2010/0273881 A1 | 10/2010 | Bar Yosef et al. |
| 2010/0298433 A1 | 11/2010 | Brenna et al. |
| 2011/0244071 A1 | 10/2011 | Bar Yoseph et al. |
| 2012/0171350 A1 | 7/2012 | Lai |
| 2012/0172442 A1 | 7/2012 | Lai |
| 2012/0172443 A1 | 7/2012 | Lai |
| 2012/0172445 A1 | 7/2012 | Lai |

FOREIGN PATENT DOCUMENTS

| | | |
|---|---|---|
| EP | 2409695 A1 | 1/2012 |
| FR | 2955459 A1 | 7/2011 |
| JP | 1175943 | 7/1989 |
| JP | 10017495 | 1/1998 |
| WO | 01/28555 | 4/2001 |
| WO | 2004/009054 | 1/2004 |
| WO | 2005/036987 | 4/2005 |
| WO | 2005063050 A1 | 7/2005 |
| WO | 2007/066232 | 6/2007 |
| WO | 2007/097523 | 8/2007 |
| WO | 2010/103374 | 9/2010 |
| WO | 2011/092299 | 4/2011 |
| WO | 2011128626 A1 | 10/2011 |
| WO | 2012/092086 | 7/2012 |
| WO | 2012/092087 | 7/2012 |
| WO | 2012/092088 | 7/2012 |
| WO | 2012/092089 | 7/2012 |
| WO | 2012/092090 | 7/2012 |

OTHER PUBLICATIONS

Venkataraman, et al., "Calcium and Phosphorus in Infant Nutrition", Nutrition in Pediatrics, edited by W. Allan Walker & B. John Watkins, Little, Brown and Company, Boston/Toronto, pp. 631-648 (1985).

Gacs, et al., "Significance of Ca-soap formation for calcium absorption in the rat," Gut, vol. 18, pp. 64-68 (1977).

Graham, et al., "Solubility of Calcium Soaps of Long-Chain Fatty Acids in Simulated Intestinal Environment," Digestive Diseases and Sciences, vol. 28(8), pp. 733-736 (1983).

Barrett-Reis, et al., "Enhanced Growth of Preterm Infants Fed a New Powdered Human Milk Fortifier: A Randomized, Controlled Trial," Pediatrics, vol. 106(3), pp. 581-588 (2000).

Pilichiewicz, et al., "Load-dependent effects of duodenal lipid on antropyloroduodenal motility, plasma CCK and PYY, and energy intake in healthy men," Am. J. Physiol. Regul. Integr. Comp. Physiol., vol. 293, pp. R2170-R2178 (2007).

Harries, "Fat Absorption in the Newborn," Acta Paediatr Scand Suppl., vol. 299, pp. 17-23 (1982).

Armand, et al., "Effect of Human Milk or Formula on Gastric Function and Fat Digestion in the Premature Infant," Pediatric Research, vol. 40(3), pp. 429-437 (1996).

Widdowson, "Absorption and Excretion of Fat, Nitrogen, and Minerals from "Filled" Milks by Babies One Week Old," The Lancet, pp. 1099-1105 (1965).

Straarup, et al., "Structured Lipids Improve Fat Absorption in Normal and Malabsorbing Rats," The Journal of Nutrition, vol. 130, pp. 2802-2808 (2000).

Tso, et al., "Randomized Structured Triglycerides Increase Lymphatic Absorption of Tocopherol and Retinol Compared with the Equivalent Physical Mixture in a Rat Model of Fat Malabsorption," The Journal of Nutrition, vol. 131, pp. 2157-2163 (2001).

Yonekura, et al., "Intestinal absorption of dietary carotenoids," Mol. Nutr. Food Res., vol. 51, pp. 107-115 (2007).

Feltrin, "Effect of fatty acid chain length on suppression of ghrelin and stimulation of PYY, GLP-2 and PP secretion in healthy men," Peptides, vol. 27, pp. 1638-1643 (2006).

Schmidt, et al., "Role of CCK in regulation of pancreaticobiliary functions and GI motility in humans: effects of loxiglumide," Am. J. Physiol., vol. 260(2 Pt. 1), G197-G206 (1991).

Ferrer, et al., "Effect of Exogenous Cholecystokinin and Secretin on Pancreatic Secretion of Insulin and Glucagon in Rats," Digestive Diseases and Sciences, vol. 46(10), pp. 2127-2133 (2001).

Foltz, et al., "Intragastric layering of lipids delays lipid absorption and increases plasma CCK but has minor effects on gastric emptying and appetite," Am. J. Physiol. Gastrointest. Liver Physiol., vol. 296(5), G982-G991 (2009).

Feltrin, et al., "Comparative effects of intraduodenal infusions of lauric and oleic acids on antropyloroduodenal motility, plasma cholecystokinin and peptide YY, appetite, and energy intake in healthy men," Am. J. Clinical Nutr., vol. 87(5), pp. 1181-1187 (2008).

Feltrin, et al., "Effects of lauric acid on upper gut motility, plasma cholecystokinin and peptide YY, and energy intake are load, but not concentration, dependent in humans," J. Physiol., vol. 581(2), pp. 767-777 (2007).

Pilichiewicz, et al., "Effects of load, and duration, of duodenal lipid on antropyloroduodenal motility, plasma CCK and PYY, and energy intake in healthy men," Am. J. Physiol. Regulatory Integrative Comp. Physiol., vol. 290(3), pp. R668-R677 (2006).

http://abbottnutrition.com/Products/oxepa, last accessed Jan. 30, 2012.

Amendment from U.S. Appl. No. 13/333,957 dated May 13, 2013.

Response to Office Action from U.S. Appl. No. 13/333,949 dated May 20, 2013.

Office Action from U.S. Appl. No. 13/333,936 dated Dec. 6, 2012.

Response to Office Action from U.S. Appl. No. 13/333,936 dated Dec. 20, 2012.

Applicant Initiated Interview Summary from U.S. Appl. No. 13/333,936 dated Dec. 28, 2012.

Non Final Office Action from U.S. Appl. No. 13/333,936 dated Mar. 15, 2013.

Office Action from U.S. Appl. No. 13/333,957 dated Jan. 18, 2013.

Office Action from U.S. Appl. No. 13/333,953 dated Jan. 2, 2013.

Amendment from U.S. Appl. No. 13/333,953 dated May 2, 2013.

Office Action from U.S. Appl. No. 13/333,949 dated Jan. 23, 2013.

Office Action from EP Application No. 11808102.5 dated Mar. 21, 2013.

Office Action from EP Application No. 11809045.5 dated Apr. 9, 2013.

Carnielli et al., "Structural Position and Amount of Palmitic Acid in Infant Formulas: Effects on Fat, Fatty Acid and Mineral Balance", J. of Pediatric Gastroenterology and Nutrition, vol. 23, ppl. 553-560 (1996).

http:// eas.com/product/pro-science-cla, last accessed on May 1, 2013.

Wikipedia article, "Rosin", http://en.wikipedia.org/wiki/Rosin (printed on Dec. 20, 2012).

International Preliminary Report on Patentability for PCT/US2011066678 dated Jul. 2, 2013.

International Preliminary Report on Patentability for PCT/US2011/066679 dated Jul. 2, 2013.

International Preliminary Report on Patentability for PCT/US2011/066680 dated Jul. 2, 2013.

International Preliminary Report on Patentability for PCT/US2011/066681 dated Jul. 2, 2013.

International Preliminary Report on Patentability for PCT/US2011/066682 dated Jul. 2, 2013.

Amendment in Response with Terminal Disclaimer to Office Action for U.S. Appl. No. 13/333,936 dated May 31, 2013.

Final Office Action from U.S. Appl. No. 13/333,936 dated Jul. 25, 2013.

Final Office Action from U.S. Appl. No. 13/333,953 dated Jun. 14, 2013.

Final Office Action from U.S. Appl. No. 13/333,957 dated Jul. 9, 2013.

Final Office Action for U.S. Appl. No. 13/333,949 dated Jul. 24, 2013.

"Gel" definition from Oxford dictionary (oxforddictionaries.com) accessed Oct. 14, 2013.

(56) References Cited

OTHER PUBLICATIONS

Amendment with RCE for U.S. Appl. No. 13/333,953 dated Oct. 14, 2013.
Response to Final Office Action for U.S. Appl. No. 13/333,949 dated Oct. 24, 2013.
Office Action from EP Application No. 11809045.5 dated Oct. 4, 2013.
Amendment with RCE for U.S. Appl. No. 13/333,957 dated Nov. 5, 2013.
Murota et al., "Uptake of micellar long-chain fatty acid and sn-2 monoacylglycerol into human intestinal Caco-2 cells exhibit characteristics of protein-mediated transport," J. Nutr., vol. 135(7), pp. 1626-1630 (2005).
Christensen et al., "Intestinal absorption and lymphatic transport of eicosapentaenoic (EPA), docosahexaenoic (DHA), and decanoic acids: dependence on intramolecular triacylglycerol structure," The American Journal of Clinical Nutrition, vol. 61, pp. 56-61 (1995).
Lien et al., "Corandomization of fats improves absorption in rats," J. Nutr., vol. 123, pp. 1859-1867 (1993).
International Search Report and Written Opinion for International Application No. PCT/US2011/066680, dated Apr. 3, 2012.
International Search Report and Written Opinion for International Application No. PCT/US2011/066682, dated Mar. 29, 2012.
International Search Report and Written Opinion for International Application No. PCT/US2011/066681, dated Mar. 30, 2012.
International Search Report and Written Opinion for International Application No. PCT/US2011/066678, dated Mar. 29, 2012.
International Search Report and Written Opinion for International Application No. PCT/US2011/066679, dated Mar. 29, 2012.
English Abstract for WO2011092299 which corresponds with FR2955459, Apr. 19, 2012.
Amendment and RCE for U.S. Appl. No. 13/333,936, filed Nov. 22, 2013.
Notice of Intention to Grant in EP Application No. 11808102.5 dated Nov. 14, 2013.
Office Action from EP Application No. 11809045.5 dated Jan. 7, 2014.
Office Action in U.S. Appl. No. 13/333,936 dated Feb. 27, 2014.
Non-final Office Action from U.S. Appl. No. 13/333,953 dated Mar. 25, 2014.
Non final rejection for U.S. Appl. No.. 13/333,957 dated Mar. 25, 2014.
Non Final Office Action for U.S. Appl. No. 13/333,949 dated Apr. 24, 2014.
First Examination Report from NZ 612,096 dated Mar. 11, 2014.

* cited by examiner

METHODS FOR IMPROVING TOLERANCE, DIGESTION, AND LIPID SOLUBLE NUTRIENT ABSORPTION IN AN INFANT, TODDLER, OR CHILD

CROSS REFERENCE TO RELATED APPLICATIONS

This application claims the benefit of U.S. Provisional Application No. 61/428,168 filed Dec. 29, 2010; U.S. Provisional Application No. 61/428,173 filed Dec. 29, 2010; U.S. Provisional Application No. 61/428,176 filed Dec. 29, 2010; U.S. Provisional Application No. 61/428,177 filed Dec. 29, 2010; and U.S. Provisional Application No. 61/428,185 filed Dec. 29, 2010, which disclosures are incorporated by reference in their entirety.

FIELD OF THE DISCLOSURE

The present disclosure relates to nutritional products comprising predigested fat and to methods for using the nutritional products. More particularly, the present disclosure relates to infant, toddler, and pediatric products comprising fatty acid-containing monoglycerides and/or a fatty acid component that provide nutritional benefits including improved digestion, tolerance, and absorption of nutrients as well as the reduction in the incidence of necrotizing enterocolitis, colic, and short bowel syndrome.

BACKGROUND OF THE DISCLOSURE

Nutritional liquids and powders, including infant and pediatric formulas, comprising a targeted selection of nutrients are well known and widely available, some of which may provide a sole source of nutrition, while others may provide a supplemental source. These nutritionals include powders that can be reconstituted with water or other aqueous liquids, as well as concentrated and ready-to-drink nutritional liquids such as milk or protein based emulsions. These nutritional liquids are especially useful when formulated with selected nutritional ingredients.

Although breast milk is generally recognized as the best nutrition for newborn infants, not every mother can successfully breastfeed. Breast milk replacers (infant formulas) may provide complete nutrition, and they have been proven to meet infant normal growth and developmental nutritional needs. Unfortunately, a small percentage of infant formula fed newborns can experience gastrointestinal (GI) intolerance problems, including loose stools, gas, necrotizing enterocolitis, colic, and the like.

The GI intolerance problem may be at least in part due to incomplete nutrient digestion and absorption in the infant. To address this tolerance problem, some infant formulas exclude lactose as an ingredient, while others replace intact milk protein with hydrolyzed protein to lessen the burden on an infant's digestion system.

Additionally, some formula fed newborn infants have a much lower fat absorption rate than the breast fed infants. This discrepancy in fat absorption rate decreases as infants become more mature. Presumably, newborn infants are deficient in lipase, and thus, they do not digest and absorb fat as well as breast fed infants who receive lipase in the mother's milk.

A preterm infant's digestion system is less developed than that of a term infant, yet they need more nutrients (calories) than term infants to foster growth and development. Medium chain triglycerides (MCT oil) are easy to digest and absorb, and have been included in preterm formulas to improve formula fat, protein and calcium absorption. The medium chain fatty acids included in the medium chain triglycerides, however, are not used to re-synthesize triglycerides to form chylomicrons after the MCT oil is digested and absorbed. As many lipid soluble nutrients, such as carotenoids and vitamins A, D, E, and K, are believed to be packaged into chylomicrons prior to entering systemic circulation, the benefit provided by MCT oil on lipid soluble nutrient absorption, which is also important for growth and development, may be more limited.

Although attempts have been made in the past to address the GI issues and others set forth above, it would be desirable to provide infant and pediatric formulas that can provide nutritional benefits similar to breast milk, and also provide good tolerance, digestion and absorption of water-insoluble hydrophobic nutrients as well as a reduction in the incidence of conditions such as necrotizing enterocolitis, colic, and short bowel syndrome. Additionally, it would be beneficial if these formulas could be stabilizer free, and specifically carrageenan free.

SUMMARY OF THE DISCLOSURE

The present disclosure is directed to nutritional products, and specifically to infant formulas, including predigested fat that includes fatty acid-containing monoglycerides and/or a fatty acid component. These nutritional compositions can advantageously be used for providing improved tolerance, digestion and absorption of nutrients, including water-insoluble/lipid soluble nutrients, and for reducing the incidence of necrotizing enterocolitis, colic, and short bowel syndrome. In some embodiments, the fatty acid component may be in fatty acid form or provided as the calcium or magnesium salts of the fatty acid, thus providing the additional benefit of additional nutrients.

One embodiment is a method for improving lipid soluble nutrient absorption in an infant, toddler, or child. The method includes administering to the infant, toddler, or child a nutritional product including at least 0.2 wt % of total dry matter of at least one of a free fatty acid component and fatty acid-containing monoglycerides.

Another embodiment is a method for improving tolerance in an infant, toddler, or child. The method includes administering to the infant, toddler, or child a nutritional product including at least 0.2 wt % of total dry matter of at least one of a free fatty acid component and fatty acid-containing monoglycerides.

Another embodiment is a method for improving digestion in an infant, toddler, or child. The method includes administering to the infant, toddler, or child a nutritional product including at least 0.2 wt % of total dry matter of at least one of a free fatty acid component and fatty acid-containing monoglycerides.

It has been discovered that nutritional products such as infant, toddler, and pediatric formulas including predigested fat, such as monoglycerides and fatty acids as described herein, can reduce the overall burden on an infant's fat digestive system to improve infant fat digestion and absorption, including water insoluble/lipid soluble nutrient absorption. Specifically, the absorption of predigested fat in the proximal part of small intestine stimulates CCK secretion, which promotes pancreatic alpha cell maturation and the secretion of digestive enzymes. Also, GLP-1 and GLP-2 secretion is stimulated, which further promotes gut maturation.

Surprisingly, the use of predigested fat and the subsequent secretion of CCK and GLP-1 retards GI transit and stimulates pancreatic enzyme secretion to allow more complete nutrient digestion and absorption. The reduction in the amount of nutrients entering the infant's colon results in reduced colonic fermentation, which is part of the cause for gas and loose stool problems. In addition, it has been discovered that the use of predigested fat can reduce the incidence of necrotizing enterocolitis, colic, and/or short bowel syndrome.

Further, it has been discovered that the unsaturated fatty acid component of the predigested fat can react with calcium or magnesium sources and the resultant formed salts are surprisingly bioavailable. Along with providing a good source of calcium or magnesium, these calcium or magnesium salts are also surprisingly bland, in contrast with fatty acids which are generally bitter and impart a strong throat burning sensation. Additionally, it has been discovered that the calcium or magnesium fatty acid salts surprisingly act to stabilize nutritional emulsions, as they do not form a hard to disperse settlement in the emulsion like many insoluble calcium salts are prone to do. As such, in many embodiments, the inclusion of calcium or magnesium fatty acid salts as part of the predigested fat may eliminate the need for stabilizers, such as carrageenan.

DETAILED DESCRIPTION OF THE DISCLOSURE

The nutritional products described herein comprise predigested fat. In many embodiments, the products include fatty acid-containing monoglycerides and a fatty acid component such that the predigested fat system includes two components. By reducing the burden on the infant, toddler, or child's digestive system, a number of benefits are realized while providing a stable, bioavailable product. These and other features of the nutritional products, as well as some of the many optional variations and additions, are described in detail hereafter.

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional product" or "nutritional composition" as used herein, are used interchangeably and, unless otherwise specified, refer to liquid and solid (including semi-liquid and semi-solid) human milk fortifiers, liquid and solid preterm infant formulas, liquid and solid infant formulas, liquid and solid follow-on formulas, liquid and solid pediatric formulas, and liquid and solid toddler formulas. The solids may be powders that may be reconstituted to form a nutritional liquid, all of which comprise one or more of fat, protein and carbohydrate and are suitable for oral consumption by a human.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spraydried and drymixed/dryblended powders.

The term "infant" as used herein, unless otherwise specified, refers to a person 12 months or younger. The term "preterm infant" as used herein, refers to an infant born prior to 36 weeks of gestation.

The term "toddler" as used herein, unless otherwise specified, refers to a person greater than one year of age to three years of age.

The term "child" as used herein, unless otherwise specified, refers to a person greater than three years of age to twelve years of age.

The term "predigested fat" as used herein, unless otherwise specified, refers to fatty acid-containing monoglycerides and/or a fatty acid component.

The term "infant formula" as used herein, unless otherwise specified, refers to liquid and solid nutritional products suitable for consumption by an infant as a main source of nutrition.

The term "preterm infant formula" as used herein, unless otherwise specified, refers to liquid and solid nutritional products suitable for consumption by a preterm infant as a main source of nutrition.

The term "human milk fortifier" as used herein, unless otherwise specified, refers to liquid and solid nutritional products suitable for mixing with breast milk or preterm infant formula or infant formula for consumption by a preterm or term infant.

The term "fatty acid-containing monoglyceride" as used herein, unless otherwise specified, refers to a glyceride consisting of one fatty acid chain covalently bonded to a glycerol molecule through an ester linkage at one of the Sn-1 ($\alpha$), Sn-2 ($\beta$), or Sn-3 ($\alpha'$) position of the glycerol molecule.

The term "fatty acid component" as used herein, unless otherwise specified, refers to free fatty acids or fatty acid salts such as calcium or magnesium fatty acid salts derived from a source having less than 20% (by weight) total myristic, palmitic, and stearic acid.

The term "lipid soluble nutrient" as used herein, unless otherwise specified, refers to water insoluble nutrients, such as oil soluble (lipid soluble) vitamins (e.g., vitamins A, D, E, and K), carotenoids (e.g., lutein, beta-carotene, lycopene, etc.), glycolipids (gangliosides), sterols, and phytochemicals.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the nutritional products of the present disclosure may also be substantially free of any optional or selected ingredient or feature described herein, provided that the remaining nutritional product still contains all of the required ingredients or features as described herein. In this context, and unless otherwise specified, the term "substantially free" means that the selected nutritional product contains less than a functional amount of the optional ingredient, typically less than 1%, including less than 0.5%, including less than 0.1%, and also including zero percent, by weight of such optional or selected ingredient.

The nutritional products and methods may comprise, consist of, or consist essentially of the elements of the products as described herein, as well as any additional or optional element described herein or otherwise useful in nutritional product and method applications.

Product Form

The predigested fat-containing nutritional products and associated methods of the present disclosure may be formulated and administered in any known or otherwise suitable oral product form. Any solid, semi-solid, liquid, semi-liquid or powder form, including combinations or variations thereof, are suitable for use herein, provided that such forms allow for safe and effective oral delivery to the individual of the ingredients as also defined herein.

The nutritional products of the present disclosure include predigested fat as described herein. The products may optionally include fatty acid-containing monoglycerides or a fatty acid component in combination with other fat sources as noted below.

The products may include any product form comprising the ingredients described herein, and which is safe and effective for oral administration. The nutritional products may be formulated to include only the ingredients described herein, or may be modified with optional ingredients to form a number of different product forms.

The nutritional products of the present disclosure are preferably formulated as dietary product forms, which are defined herein as those embodiments comprising the ingredients of the present disclosure in a product form that then contains at least one of fat, protein, and carbohydrate, and preferably also contains vitamins, minerals, or combinations thereof. In many embodiments, the product will comprise predigested fat in combination with protein, carbohydrate, vitamins, and minerals to produce a nutritional product.

The nutritional products may be formulated with sufficient kinds and amounts of nutrients to provide a sole, primary, or supplemental source of nutrition, or to provide a specialized nutritional product for use in individuals afflicted with specific diseases or conditions or with a targeted nutritional benefit.

Specific non-limiting examples of product forms suitable for use with the predigested fat as disclosed herein include, for example, liquid and powdered human milk fortifiers, liquid and powdered preterm infant formulas, liquid and powdered infant formulas, liquid and powdered elemental and semi-elemental formulas, liquid and powdered pediatric formulas, and liquid and powdered toddler formulas.

Nutritional Liquids

Nutritional liquids include both concentrated and ready-to-feed nutritional liquids. These nutritional liquids are most typically formulated as suspensions or emulsions.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 88%, of water by weight of the nutritional emulsions. The nutritional emulsions may have a variety of product densities, but most typically have a density greater than about 1.03 g/ml, including greater than about 1.04 g/ml, including greater than about 1.055 g/ml, including from about 1.06 g/ml to about 1.12 g/ml, and also including from about 1.085 g/ml to about 1.10 g/ml.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz (740-810 kcal/liter) formulas are more commonly used in preterm or low birth weight infants, and the 20-21 kcal/fl oz (675-680 to 700 kcal/liter) formulas are more often used in term infants. In some embodiments, the emulsion may have a caloric density of from about 100 kcal/liter to about 660 kcal/liter, including from about 150 kcal/liter to about 500 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 2 mL, or even at least about 5 mL, or even at least about 10 mL, or even at least about 25 ml, including ranges from about 2 mL to about 300 mL, including from about 4 mL to about 250 mL, and including from about 10 mL to about 240 mL.

As noted above, the nutritional products may also be in the form of a semi-liquid, which includes those forms that are intermediate in properties, such as flow properties, between liquids and solids. Exemplary semi-liquids include thick shakes and liquid gels.

Nutritional Solids

The nutritional solids may be in any solid form but are typically in the form of flowable or substantially flowable particulate compositions, or at least particulate compositions. Particularly suitable nutritional solid product forms include spray dried, agglomerated or dryblended powder compositions. The compositions can easily be scooped and measured with a spoon or similar other device, wherein the compositions can easily be reconstituted by the intended user with a suitable aqueous liquid, typically water, to form a nutritional formulation for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz (740-810 kcal/liter) formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50 kcal/liter to about 660 kcal/liter, including from about 100 kcal/liter to about 500 kcal/liter.

As noted above, the nutritional products may also be in the form of a semi-solid, which includes those forms that are intermediate in properties, such as rigidity, between solids and liquids. Some semi-solid examples include puddings, gelatins, and doughs.

Predigested Fat System

A. Fatty Acid-Containing Monoglycerides

In some embodiments, the nutritional products of the present disclosure include fatty acid-containing monoglycerides, also known as monoacylglycerols, alone or in combination with a fatty acid component as described below. Monoglycerides are normal metabolites in the body formed during the breakdown of triglycerides and diglycerides. As noted, the fatty acid-containing monoglycerides may be included in the nutritional products in combination with a fatty acid component, such as fatty acids and/or fatty acid salts as described below, or may be included in the nutritional products in the absence of the fatty acid component.

Suitable fatty acid-containing monoglycerides for use in the nutritional products may include fatty acids having a chain length of from 4 to 22 carbon atoms, including fatty acids having a chain length of from 14 to 20 carbon atoms, and including palmitic acid (16 carbon atoms). Particularly preferred are monoglycerides wherein at least 70% of the fatty acids in the monoglycerides are at the Sn-1 position, including monoglycerol palmitate having at least about 70% of the palmitic acid residues at the Sn-1 position (also referred to as the alpha position), including at least about 80% at the Sn-1 position, and including from about 85% to about 100% in the Sn-1 position. Further, in some embodiments, the monoglycerides included in the nutritional products described herein may include trace amounts of diglycerides, free glycerol, and/or free fatty acids. As used herein, the term "trace amounts" means amounts not exceeding 10 wt %, but more commonly less than 7.5 wt %.

In one specific embodiment, the monoglycerides (and optionally the fatty acid component as discussed below) in the nutritional product are partially or totally provided to the product through the use of hydrolyzed lard or hydrolyzed tallow. Lard, tallow, and other animal based products, can be added to the nutritional product and hydrolyzed into monoglycerides and fatty acids by pancreatic lipase. Alternatively, the lard or tallow can be hydrolyzed prior to incorporation into the nutritional product to produce monoglycerides and fatty acids, which can be introduced into the nutritional product. Lard, tallow, or hydrolyzed lard or tallow, can provide a portion or all of the monoglycerides and/or fatty acids in the nutritional product.

In another embodiment, the monoglycerides in the nutritional product are partially or totally derived from oils such as vegetable oils, marine oils, fish oils, algae oil, fungal oils, tree resin, and combinations thereof. Suitable vegetable oils include, for example, olive oil, canola oil, corn oil, palm oil, soybean oil, and combinations thereof.

The fatty acid-containing monoglycerides are present in the nutritional products in amounts of at least about 10% by weight of the fat component included in the nutritional product, including at least about 15% by weight of the fat component included in the nutritional product, including at least about 20% by weight of the fat component included in the nutritional product, including from 12% to 45%, including from 15% to 25%, and including about 10%, including about 15%, including about 20%, including about 25%, including about 30%, and further including about 35%, or even about 40%, or even about 50%, or even about 60%, or even about 70%, or even about 80%, or even about 90%, or even about 100% by weight of the fat component included in the nutritional product.

In one specific embodiment when the nutritional product is a nutritional powder including a fat component of about 28% (by weight of the nutritional powder), the fatty acid-containing monoglycerides are present at a level of about 10% (by weight of the fat component), or about 2.8 grams of fatty acid-containing monoglycerides per 100 grams of nutritional powder.

In another specific embodiment when the nutritional product is a ready-to-feed nutritional liquid including a fat component of about 3.67% (by weight of the ready-to-feed nutritional liquid), the fatty acid-containing monoglycerides are present at a level of about 10% (by weight of the fat component), or about 0.367 grams of fatty acid-containing monoglycerides per 100 grams of ready-to-feed nutritional liquid.

In another specific embodiment when the nutritional product is a concentrated nutritional liquid including a fat component of about 7.34% (by weight of the concentrated nutritional liquid), the fatty acid-containing monoglycerides are present at a level of about 10% (by weight of the fat component), or about 0.734 grams of fatty acid-containing monoglycerides per 100 grams of concentrated nutritional liquid.

In addition to providing the numerous benefits outlined above, the fatty acid-containing monoglycerides also have been found to have antiviral and/or antibacterial activity in the nutritional products. Specifically, the presence of fatty acid-containing monoglycerides in nutritional products has been found to kill pathogens and/or slow their replication.

B. Fatty Acid Component

In addition to, or in place of, the fatty acid-containing monoglycerides described above, the nutritional products of the present disclosure may include a fatty acid component comprising fatty acids as a part of the predigested fat system. Fatty acids are normal metabolites in the body notably formed during the breakdown of fat (triglycerides, diglycerides, cholesterol esters, and certain phospholipids). This fatty acid component is separate and distinct from the fatty acid-containing monoglycerides discussed above.

Any fatty acid beneficial in a nutritional product can be included in the nutritional products as part of the predigested fat system. In one embodiment, the fatty acid is an unsaturated free fatty acid. In some embodiments including unsaturated free fatty acids, the total amount of saturated free fatty acids with a chain length of longer than 14 carbon atoms is less than 15 wt %. Exemplary fatty acids suitable for inclusion in the nutritional products described herein include, but are not limited to, arachidonic acid, linolenic acid, docosahexaenoic acid, stearidonic acid, oleic acid, eicosenoic acid, mead acid, erucic acid, nervonic acid, and mixtures and combinations thereof. Particularly preferred fatty acids include arachidonic acid, linoleic acid, linolenic acid, docosahexaenoic acid, and oleic acid.

The fatty acid component for inclusion in the predigested fat system include those derived from oils such as vegetable oils, marine oils, fish oils, algae oil, fungal oils, animal fats, fractionated animal fats and combinations thereof. Suitable vegetable oils include, for example, olive oil, canola oil, corn oil, soybean oil, and combinations thereof. In one embodiment, when animal fat is used, the fatty acids are derived by enzymatic hydrolysis of lard or tallow and the level of palmitic and stearic acid in the resultant fatty acid mixture is reduced to less than 20% of the total fatty acids, including less than 2% of the total fatty acids. In another embodiment, at least some of the fatty acids are derived from soybean oil or tree resin. Once derived from the oil source, the fatty acids are substantially free of monoglycerides, diglycerides and triglycerides.

Generally, the fatty acids will be derived from a source oil that contains less than about 20% (by weight) palmitic acid and/or stearic acid and/or myristic acid. In some embodiments the fatty acids will be derived from a source oil that contains less than about 15% (by weight), including less than about 10% (by weight), including less than about 5% (by weight), and including less than about 2% (by weight) palmitic acid and/or stearic acid and/or myristic acid.

In one specific embodiment, the fatty acids are derived from a source oil that contains less than about 20% (by weight), including from about 10% (by weight) to about 15% (by weight) palmitic acid and/or stearic acid and/or myristic acid. In another specific embodiment, the nutritional product includes palmitic acid in an amount of less than about 10% (by weight) of the total fatty acids.

In some embodiments, the nutritional products may include the fatty acids in salt form; that is, the fatty acids may be added into the nutritional products as fatty acid salts. In one suitable embodiment, the fatty acids are added to the nutritional product in the form of calcium fatty acid salts, magnesium fatty acid salts or a combination thereof.

The fatty acids salt can be prepared by one skilled in the art based on the disclosure herein. In one suitable process, emulsions that include $C_{10}$-$C_{24}$ fatty acid calcium salts can be prepared by first preparing the fatty acid salts by using several starting sources of calcium mixed with at least one source of $C_{10}$-$C_{24}$ fatty acids. More particularly, in one method, a starting source comprising $C_{10}$-$C_{24}$ fatty acids in a blend of triglycerides or free form can be formed by contact with calcium hydroxide and/or calcium carbonate and/or calcium phosphate. In another method, $C_{10}$-$C_{24}$ fatty acids in a triglyceride blend or in free form can be made by contact with hydrated $CaCl_2$ or $Ca(AcO)_2$ at a pH of 6 to about 7.5.

The above methods can be conducted under an inert atmosphere, e.g., under $N_2$ or argon. In other examples, any of the disclosed methods can be conducted under an ambient atmosphere (e.g., wherein the reaction is not conducted under a low oxygen atmosphere).

The source comprising the $C_{10}$-$C_{24}$ fatty acids and calcium source can be mixed by any methods known in the art. "Mixing" is not meant to imply a particular outcome of mixing, such as the dissolution of any components to a particular level or the formation of a particular composition, such as homogeneous mixture, although such mixtures can be produced and some components can be dissolved by mixing. Mixing can be vigorous and can be performed manually or by a mechanical device such as, but not limited to, a static mixer, a magnetic stirrer, a shaker, spinner, or rotating device. Mixing can be performed by forcing or bubbling a gas through the mixture or by sonication.

Mixing the source of $C_{10}$-$C_{24}$ fatty acids with a calcium source can be performed for at least 1 minute. Mixing can also be performed for at least 1, 5, 15, 20, 25, 30, 35, 40, 45, 50, 55, 60, 65, 70, 75, 80, 85, 90, 95, or 100 minutes, where any of the stated values can form an upper or lower endpoint as appropriate.

Mixing can be performed at various temperatures, but, typically, the method takes place at an elevated temperature. The precise elevated temperature may depend on the particular starting sources of $C_{10}$-$C_{24}$ fatty acids or calcium and amounts thereof being used. Suitable temperatures at which the disclosed mixing can be performed include, but are not limited to, from about 4 to about 100° C., from about 10 to about 100° C., from about 15 to about 100° C., or from about 20 to about 70° C.

The sources comprising $C_{10}$-$C_{24}$ fatty acids or calcium may also be heated prior to mixing. Such a pre-heating step can be performed at any of the temperatures or temperature ranges described herein.

In some embodiments, mixing of the $C_{10}$-$C_{24}$ fatty acids and calcium can be conducted under reduced pressure. A suitable pressure is less than or equal to about 1 Torr or less than or equal to about 0.1 Torr.

In one desirable embodiment, the $C_{10}$-$C_{24}$ fatty acid calcium salts are prepared by adding free $C_{10}$-$C_{24}$ unsaturated fatty acids and a calcium source, such as $Ca(OH)_2$, $CaCl_2$, $CaCO_3$, Ca-citrate or a mixture of these salts, to form an oil blend. More particularly, the fatty acids are dissolved in a warm aqueous solution (e.g., having a temperature of from about 40 to about 80° C.). The pH of the solution may be adjusted, typically to a pH of about 10-11, using KOH or NaOH. Calcium is then added to the dissolved fatty acid-containing solution. Typically, the fatty acids and calcium are allowed to sit for 10 minutes to ensure a complete reaction between the fatty acids and the calcium ions. The mixture is then homogenized to form the oil blend.

In another desirable embodiment, a mixture of calcium fatty acid salts including fatty acids from fish oil, algae oil, fungal oil, and soy oil is prepared as part of the predigested fat system. The fish oil, algae oil, fungal oil and soy oil are mixed together and hydrolyzed by potassium hydroxide under a nitrogen blanket. A calcium source, such as calcium chloride, is then added to the mixture to react with the fatty acids to produce insoluble calcium fatty acids salts. The insoluble fatty acid salts can be isolated by filtering, and washed with water prior to vacuum drying.

It has surprisingly been found that although fatty acid salts, such as calcium fatty acid salts, are generally insoluble in nutritional products, they do not settle in solution to form a layer of hard-to-redisperse sediment. Thus, the use of calcium and/or magnesium fatty acid salts allows for better calcium/magnesium delivery and, in many embodiments, may eliminate the need for additional stabilizers, such as carrageenan, such that the product can be substantially or completely "carrageenan free."

Accordingly, the use of fatty acid salts allows for improved calcium and/or magnesium and fatty acid bioavailability as compared to products using calcium phosphate or calcium carbonate at the calcium source.

Moreover, it has been found that the use of the fatty acid salts in the nutritional products of the present disclosure provides bioavailable fatty acids such as arachidonic acid (ARA) and the like, which are shown to enhance the growth of infants. The use of the predigested fat also provides a creamy nutritional product with improved product stability and longer shelf life.

The nutritional products generally include fatty acids or fatty acid salts in an amount of at least about 10% (by weight) of the fat component included in the nutritional product, including at least about 15%, including at least about 20%, including from about 10% to about 60%, including from about 15% to about 40%, and including from about 15% to about 35%, including about 10%, including about 15%, including about 20%, including about 25%, including about 30%, including about 35%, and further including about 40%, or even about 50%, or even about 60%, or even about 70%, or even about 80%, or even about 90%, or even about 100% by weight of the fat component included in the nutritional product.

In some embodiments, the nutritional products include a mixture of a fatty acid component and fatty-acid containing monoglycerides. In these embodiments, the nutritional product contains the mixture in an amount of at least 10% (by weight) of the fat component included in the nutritional product, including at least about 15%, including at least about 20%, including from about 10% to about 40%, including from about 20% to about 65%, including from about 25% to about 50%, including from about 15% to about 30%, and including from about 15% to about 25%, including about 10%, including about 15%, including about 20%, including about 25%, including about 30%, including about 35%, and further including about 40% or even about 50%, or even about 60%, or even about 70%, or even about 80%, or even about 90%, or even about 100% by weight of the fat component included in the nutritional product.

In other embodiments, the nutritional products include a fatty acid component, fatty-acid containing monoglycerides, or combinations thereof in an amount of at least 0.2% (by weight), including at least 1% (by weight), including at least 2% (by weight), and including at least 5% (by weight) of total dry matter in the nutritional product.

Macronutrients

Although total concentrations or amounts of the fat, protein, and carbohydrates may vary depending upon the product type (i.e., human milk fortifier, infant formula, etc.), product form (i.e., nutritional solid, powder, ready-to-feed liquid, or concentrated liquid) and targeted dietary needs of the intended user, such concentrations or amounts most typically fall within one of the following embodied ranges, inclusive of any other fat, protein, and/or carbohydrate ingredients as described herein.

For the liquid preterm and term infant formula products, carbohydrate concentrations most typically range from about 5% to about 40%, including from about 7% to about 30%, including from about 10% to about 25%, by weight of the preterm or term infant formula; fat concentrations (including both predigested fat and any other fat sources) most typically range from about 1% to about 30%, including from about 2% to about 15%, and also including from about 3% to about 10%, by weight of the preterm or term infant formula; and protein concentrations most typically range from about 0.5% to about 30%, including from about 1% to about 15%, and also including from about 2% to about 10%, by weight of the preterm or term infant formula.

For the liquid human milk fortifier products carbohydrate, concentrations most typically range from about 10% to about 75%, including from about 10% to about 50%, including from about 20% to about 40%, by weight of the human milk fortifier; fat concentrations (including both predigested fat and any other fat sources) most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

The level or amount of carbohydrates, fats, and/or proteins in the liquid nutritional products may also be characterized in addition to or in the alternative as a percentage of total calories in the nutritional products as set forth in the following Table. These macronutrients for liquid nutritional products of the present disclosure are most typically formulated within any of the caloric ranges (embodiments A-F) described in the following Table (each numerical value is preceded by the term "about").

| Nutrient % Total Cal. | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |

| Nutrient % Total Cal. | Embodiment D | Embodiment E | Embodiment F |
|---|---|---|---|
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following Table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, and including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, and including from about 20% to about 50% by weight of the human milk fortifier.

The total amount or concentration of fat, carbohydrate, and protein, in the powdered nutritional products of the present disclosure can vary considerably depending upon the selected product and dietary or medical needs of the intended user. Additional suitable examples of macronutrient concentrations are set forth below. In this context, the total amount or concentration refers to all fat, carbohydrate, and protein sources in the powdered product. For powdered nutritional products, such total amounts or concentrations are most typically and preferably formulated within any of the embodied ranges described in the following Table (all numbers have "about" in front of them).

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional products of the present disclosure may, in addition to predigested fat, comprise an additional source or sources of fat (the total amount of fat being referred to herein as the "fat component" or "fat system" of the nutritional product). Suitable additional sources of fat for use herein include any fat or fat source that is suitable for use in an oral nutritional product and is compatible with the elements and features of such products.

Non-limiting examples of suitable additional fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof. In one embodiment, suitable fats or sources thereof include oils and oil blends including long chain polyunsaturated fatty acids (LC-PUFAs), preferably LC-PUFAs having four or more double bonds. Some non-limiting specific polyunsaturated acids for inclusion include, for example, docosahexaenoic acid (DHA), arachidonic acid (ARA), eicosapentaenoic acid (EPA), and the like.

Generally, the predigested fat described herein is included in the nutritional product in combination with one, two, three, four, or more additional fat sources. In one embodiment, monoglycerides (desirably in the form of monoglycerol palmitate), fatty acids (desirably in the form of calcium salts), a high oleic oil, and coconut oil are combined together to provide the fat component in a nutritional product. In this embodiment, the monoglycerides are present in an amount of from about 1% to about 40%, including from about 10% to about 30%, including about 10%, about 15%, about 20%, about 23%, and about 25% by weight of the fat component, the fatty acids are present in an amount of from about 1% to about 40%, including from about 10% to about 30%, including about 10%, about 15%, about 20%, and about 25% by weight of the fat component, the high oleic oil is present in an amount of from about 1% to about 40%, including from about 10% to about 30%, including about 10%, about 15%, about 20%, about 25%, and about 30% by weight of the fat component, and the coconut oil is present in an amount of from about 1% to about 40%, including from about 10% to about 30%, including about 10%, about 15%, about 17%, about 20%, and about 25% by weight of the fat component.

In another embodiment, fatty acid-containing monoglycerides (desirably in the form of monoglycerol palmitate), a fatty acid component (desirably in the form of calcium salts), a high oleic safflower oil, and coconut oil are combined together to provide the fat component in a nutritional product. In this embodiment, the monoglycerides are present in an amount of from about 1% to about 40%, including from about 10% to about 30%, including about 10%, about 15%, about 20%, about 23% and about 25% by weight of the fat component, the fatty acids are present in an amount of from about 1% to about 40%, including from about 10% to about 30%, including about 10%, about 15%, about 20%, and about 25% by weight of the fat component, the high oleic oil is present in an amount of from about 1% to about 40%, including from about 10% to about 30%, including about 10%, about 15%, about 20%, about 25%, and about 30% by weight of the fat component, and the coconut oil is present in an amount of from about 1% to about 40%, including from about 10% to about 30%, including about 10%, about 15%, about 17%, about 20%, and about 25% by weight of the fat component.

In another embodiment, fatty acid-containing monoglycerides (desirably in the form of monoglycerol palmitate), a fatty acid component (desirably in the form of calcium salts), a high oleic safflower oil, coconut oil, DHA-containing oil, and ARA-containing oil are combined together to provide the fat component in a nutritional product. In this embodiment, the monoglycerides are present in an amount of from about 1% to about 40%, including from about 10% to about 30%, including about 10%, about 15%, about 20%, about 23%, and about 25% by weight of the fat component, the fatty acids are present in an amount of from about 1% to about 40%, including from about 10% to about 30%, including about 10%, about 15%, about 20%, and about 25% by weight of the fat component, the high oleic oil is present in an amount of from about 1% to about 40%, including from about 10% to about 30%, including about 10%, about 15%, about 20%, about 25%, and about 30% by weight of the fat component, and the coconut oil is present in an amount of from about 1% to about 40%, including from about 10% to about 30%, including about 10%, about 15%, about 17%, about 20%, and about 25% by weight of the fat component. The DHA-containing oil is present in an amount of from about 1% to about 10%, including about 5% by weight of the fat component and the ARA-containing oil is present in an amount of from about 1% to about 10%, including about 5% by weight of the fat component.

In another embodiment, the fat component comprises about 38% (by weight) high oleic safflower oil, about 17% (by weight) coconut oil, about 23% (by weight) monoglycerol palmitate, about 20% (by weight) calcium fatty acid salts, about 0.5% (by weight) DHA-containing oil, and about 1.0% (by weight) ARA-containing oil.

Protein

The nutritional products of the present disclosure may optionally further comprise protein in addition to the predigested fat. Any protein source that is suitable for use in oral nutritional products and is compatible with the elements and features of such products is suitable for use in combination with the predigested fat.

Non-limiting examples of suitable protein or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium castanets, whole cow milk, partially or completely defatted milk, soy protein isolates, soy protein concentrates, and so forth.

Carbohydrate

The nutritional products of the present disclosure may further optionally comprise any carbohydrates that are suitable for use in an oral nutritional product and are compatible with the elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof.

Other Optional Ingredients

The nutritional products of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the ingredients in the selected product form.

Non-limiting examples of such optional ingredients include preservatives, anti-oxidants, emulsifying agents, buffers, fructooligosaccharides, galactooligosaccharides, prebiotics, pharmaceutical actives, additional nutrients as described herein, colorants, flavors, thickening agents and stabilizers, emulsifying agents, lubricants, and so forth.

The nutritional products may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from 0.1% to about 10%, and also including from about 1% to about 6%, by weight of the nutritional product. Optional artificial sweetener concentrations may range from about 0.01%, including from about 0.05% to about 5%, also including from about 0.1% to about 1.0%, by weight of the nutritional product.

A flowing agent or anti-caking agent may be included in the nutritional products as described herein to retard clumping or caking of the powder over time and to make a powder embodiment flow easily from its container. Any known flowing or anti-caking agents that are known or otherwise suitable for use in a nutritional powder or product form are suitable for use herein, non limiting examples of which include tricalcium phosphate, silicates, and combinations thereof. The concentration of the flowing agent or anti-caking agent in the nutritional product varies depending upon the product form, the other selected ingredients, the desired flow properties, and so forth, but most typically range from about 0.1% to about 4%, including from about 0.5% to about 2%, by weight of the nutritional product.

A stabilizer may also be included in the nutritional products. Any stabilizer that is known or otherwise suitable for use in a nutritional product is also suitable for use herein, some non-limiting examples of which include carrageenan and gums such as xanthan gum. The stabilizer may represent from about 0.1% to about 5.0%, including from about 0.5% to about 3%, including from about 0.7% to about 1.5%, by weight of the nutritional product.

The nutritional products compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional products may further comprise any of a variety of other additional minerals, non-limiting examples of which include calcium, phosphorus, magnesium, iron, zinc, manganese, copper, sodium, potassium, molybdenum, chromium, chloride, and combinations thereof. Further, in some embodiments, the nutritional products may be free of carrageenan.

Methods of Manufacture

The nutritional products of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional products described herein.

The nutritional products of the present disclosure can therefore be prepared by any of a variety of known or otherwise effective product or manufacturing methods. In one suitable manufacturing process, for example, at least three separate slurries are prepared, including a protein-in-fat (PIF) slurry, a carbohydrate-mineral (CHO-MN) slurry, and a protein-in-water (PIW) slurry. The PIF slurry is formed by heating and mixing the oil (e.g., monoglyceride and/or fatty acids, fatty acid containing oil, canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), and/or thickening or suspending agents (e.g., avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., fructooligosaccharide, sucrose, corn syrup, etc.). The PIW slurry is then formed by mixing with heat and agitation the remaining protein, if any.

In one specific embodiment of the present disclosure, all, or a portion of, the predigested fat included in the nutritional product can be added to the CHO-MIN slurry, which contains less than 5% (by weight of the CHO-MIN slurry) of fat in the form of triglycerides. In this embodiment, at least 5% (by weight) of the total fat present in the nutritional product is in the form of predigested fat and is added to the CHO-MIN slurry. In some embodiments, at least 5% (by weight), including at least 10% (by weight), including at least 20% (by weight), including at least 30% (by weight), including at least 40% (by weight), including at least 50% (by weight), including at least 60% (by weight), including at least 70% (by weight), including at least 80% (by weight), including at least 90% (by weight), and including 100% (by weight) of the total predigested fat included in the nutritional product is added to the CHO-MIN slurry. In one particular embodiment, lipid soluble nutrients, such as mixed carotenoids or vitamins A, D, E, and K, are dissolved in the predigested fat prior to the predigested fat being added to the CHO-MIN slurry or during the manufacture of the CHO-MIN slurry. By adding the predigested fat to the CHO-MIN slurry as opposed to the PIF slurry, the stability of the finished nutritional composition can be improved.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can also be filled and then sterilized to form a ready-to-feed or concentrated liquid, or it can be spray dried, drymixed and/or agglomerated.

The nutritional solid, such as a spray dried nutritional powder or dry-mixed nutritional powder, may be prepared by any collection of known or otherwise effective techniques suitable for making and formulating a nutritional powder.

For example, when the nutritional powder is a spray-dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, dry mixing, or otherwise adding additional nutritional ingredients, including any one or more of the ingredients described herein, to the spray dried nutritional powder.

Other suitable methods for making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), and U.S. Patent Application 20030118703 A1 (Nguyen, et al.), which descriptions are incorporated herein by reference to the extent that they are consistent herewith.

Methods of Use

In accordance with the present disclosure, and as further described below, the nutritional products described herein can be utilized for a number of purposes including, for example, improving digestion, improving nutrient absorption, improving tolerance, decreasing the incidence of necrotizing enterocolitis, decreasing the incidence of colic, and decreasing the incidence of short bowel syndrome. The individual (infant, toddler, or child) utilizing the nutritional products described herein may actually have or be afflicted with the disease or condition described (i.e., may actually have digestion, nutrient absorption and/or tolerance problems or may actually have necrotizing enterocolitis, colic, or short bowel syndrome), or may be susceptible to, or at risk of, getting the disease or condition (that is, may not actually yet have the disease or condition, but is at elevated risk as compared to the general population for getting it due to certain conditions, family history, etc.) Whether the individual actually has the disease or condition, or is at risk or susceptible to the disease or condition, the individual is classified herein as "in need of" assistance in dealing with and combating the disease or condition. For example, an infant may actually have necrotizing enterocolitis or may be at risk of getting necrotizing enterocolitis (susceptible to getting necrotizing enterocolitis) due to premature birth. Similarly, in another example, an infant may actually have tolerance and/or digestion and/or nutrient absorption issues, or may be at risk of (susceptible to) getting one or more of these conditions due to having other diseases or conditions, or a family history of such problems. Whether the individual actually has the disease or condition, or is only at risk of or susceptible to getting the disease or condition, it is within the scope of the present disclosure to assist the individual with the nutritional products described herein.

Based on the forgoing, because some of the method embodiments of the present disclosure are directed to specific subsets or subclasses of identified individuals (that is, the subset or subclass of individuals "in need" of assistance in addressing one or more specific diseases or specific conditions noted herein), not all individuals can benefit from all method embodiments described herein as not all individuals will fall within the subset or subclass of individuals as described herein for certain diseases or conditions.

The nutritional products as described herein comprise predigested fat desirably in combination with one or more additional fat sources to provide a nutritional source for infants, toddlers, and children for improving digestion and absorption of nutrients. Specifically, similar to the digestion of breast fed infants, as the fat source is at least partially digested prior to entering the duodenum, more time is allowed for the nutrients to be absorbed by the infant, particularly in the intestines, and the amount of nutrients that enter the infant's colon is reduced, thus resulting in less nutrients that can be fermented and produce gas, which can result in reduced tolerance of a product. As such, by utilizing a predigested fat source such as monoglycerides and/or fatty acids in a nutritional product, such as an infant formula, it is now possible to provide infants with an alternative, or supplement, to breast milk that more closely mimics the benefits thereof.

Along with improved absorption of nutrients as described above, it has been found that the use of predigested fat within a nutritional product also facilitates formation of micelles when administered with one or more water insoluble hydrophobic compounds, such as oil soluble (lipid soluble) vitamins (vitamins A, D, E, and K), carotenoids (e.g., lutein, beta-carotene licopene etc.), glycolipids (gangliosides), sterols, and phytochemicals. Formation of these micelles allows the insoluble hydrophobic compounds to be dissolved into digesta, which is a step for absorption by the villi of the intestine. In addition, the predigested fat will be used to re-synthesize triglycerides to form chylomicron. Chylomicron carries the water insoluble hydrophobic compounds into the lymph, wherein circulation transports the insoluble hydrophobic compounds to the targeted organs and/or tissues to produce desired physiological effects.

In addition to the benefits discussed above, it has been discovered that nutritional products including predigested fat stimulate cholecystokinin (CCK) production in the duodenum, which stimulates pancreatic lipase production. This production results in further digestion of nutrients and reduces upper gastrointestinal contractions, which allows more time for absorption. Thus, the use of predigested fat in the nutritional products reduces the total amount of nutrients that enter the colon, which can be fermented and produce gas and a bloated feeling. As such, the use of predigested fats in nutritional products can improve tolerance by improving nutrient digestion and absorption with less gas. This can be particularly important with infants, as tolerance can be an issue in some infants.

Along with stimulating CCK production, it has been discovered that predigested fat also induces secretion of the intestinal growth hormone, Glucagon-like peptide-2 (GLP-2). GLP-2 can enhance the maturation of the infant's gut, which results in better digestion and nutrient absorption.

It has further been found that the nutritional products as described herein comprising predigested fat can be used to provide a nutritional source for infants, toddlers, or children that may reduce the incidence of necrotizing enterocolitis (NEC), colic, and/or short bowel syndrome.

In addition, in embodiments where the nutritional product is manufactured by a process in which at least a portion of the predigested fat (or in some embodiments all of the predigested fat) is added to the carbohydrate-mineral slurry as opposed to the protein in fat slurry, the resulting stability of the nutritional product (generally in the form of a nutritional emulsion) may be improved.

EXAMPLES

The following examples illustrate specific embodiments and/or features of the nutritional products of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional products prepared in accordance with the manufacturing methods described herein, such that each exemplified product, unless otherwise specified, includes an aseptically processed embodiment and a retort packaged embodiment.

The nutritional liquid embodiments are aqueous oil-in-water emulsions that are packaged in 240 ml plastic containers and remain physically stable for 12-18 months after formulation/packaging at storage temperatures ranging from 1-25° C.

Examples 1-4

Examples 1-4 illustrate lactose-free infant nutritional emulsions of the present disclosure, the ingredients of which are listed in the Table below. All ingredient amounts are listed as kilogram per 1000 kilogram batch of product, unless otherwise specified.

| Ingredient | Example 1 | Example 2 | Example 3 | Example 4 |
|---|---|---|---|---|
| Water | Q.S | Q.S. | Q.S. | Q.S. |
| Maltodextrin | 53 | 43.3 | 50 | 60 |
| Sucrose | 16.5 | 25 | 19.2 | 16.38 |
| Milk Protein isolate | 15.65 | 15.65 | 15.65 | 15.65 |
| Corn Oil | 12 | 12 | 12 | 12 |
| High Oleic Safflower Oil | 10 | 10 | 10 | 10 |
| Monoglycerol Palmitate | 10 | 9 | 8 | 7 |
| $C_{10}$-$C_{24}$ fatty acid calcium salt | 6.0 | 7 | 8 | 9 |
| Coconut oil | 2 | 2 | 2 | 2 |
| Fungal oil | 0.3 | 0.3 | 0.3 | 0.3 |
| Lecithin | 0.1 | 0.1 | 0.1 | 0.1 |
| Potassium phosphate dibasic | 0.96 | 0.96 | 0.96 | 0.96 |
| Potassium chloride | 0.3 | 0.3 | 0.3 | 0.3 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |

Examples 5-8

Examples 5-8 illustrate lactose-based nutritional emulsions of the present disclosure, the ingredients of which are listed in the Table below. All ingredient amounts are listed as kg per 1000 kg batch of product, unless otherwise specified.

| Ingredient | Example 5 | Example 6 | Example 7 | Example 8 |
|---|---|---|---|---|
| Water | Q.S | Q.S. | Q.S. | Q.S. |
| Lactose | 58 | 66 | 71 | 63 |
| Non-fat Dry Milk | 25 | 10 | 0 | 16 |
| Whey Protein Concentrate | 6.4 | 13 | 18 | 10.5 |
| High Oleic Safflower Oil | 14 | 14 | 14 | 14 |
| Coconut Oil | 6.2 | 6.2 | 6.2 | 6.2 |
| Monoglycerol Palmitate | 10 | 8 | 6 | 4 |
| $C_{10}$-$C_{24}$ Fatty Acids | 5.5 | 7.5 | 9.5 | 11.5 |
| Fructooligosaccharides/Galacto-oligosaccharides | 9 | 9 | 9 | 9 |
| Fungal Oil | 0.3 | 0.3 | 0.3 | 0.3 |
| Potassium Phosphate Dibasic | 0.96 | 0.96 | 0.96 | 0.96 |
| Calcium Hydroxide | 0.78 | 1.07 | 1.36 | 1.64 |
| Potassium Chloride | 0.3 | 0.3 | 0.3 | 0.3 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Vitamin A, D, E Premix | 0.0758 | 0.0758 | 0.0758 | 0.0758 |
| Water sol. Vitamin Premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |

Examples 9-12

Examples 9-12 illustrate soy-based infant nutritional emulsions of the present disclosure, the ingredients of which are listed in the Table below. All ingredient amounts are listed as kilogram per 1000 kilogram batch of product, unless otherwise specified.

| Ingredient | Example 9 | Example 10 | Example 11 | Example 12 |
|---|---|---|---|---|
| Water | Q.S | Q.S. | Q.S. | Q.S. |
| Corn Syrup Solids | 53 | 43.3 | 50 | 60 |
| Sucrose | 16.5 | 25 | 19.2 | 16.38 |
| Soy Protein Isolate | 19.5 | 19.5 | 19.5 | 19.5 |
| Corn Oil | 12 | 12 | 12 | 12 |
| High Oleic Safflower Oil | 10 | 10 | 10 | 10 |
| Monoglycerol Palmitate | 10 | 9 | 8 | 7 |
| $C_{10}$-$C_{24}$ Fatty Acids | 6.0 | 7 | 8.0 | 9 |
| Fungal Oil | 0.3 | 0.3 | 0.3 | 0.3 |
| L-cystine | 2.3 | 2.3 | 2.3 | 2.3 |
| L-tyrosine | 1.1 | 1.1 | 1.1 | 1.1 |
| Calcium Hydroxide | 0.09 | 1.0 | 1.1 | 1.2 |
| L-tryptophan | 0.66 | 0.66 | 0.66 | 0.66 |
| Potassium Phosphate Dibasic | 0.96 | 0.96 | 0.96 | 0.96 |
| Potassium Chloride | 0.3 | 0.3 | 0.3 | 0.3 |
| Ascorbic Acid | 0.235 | 0.235 | 0.235 | 0.235 |
| Carrageenan | 0.150 | 0.150 | 0.0 | 0.0 |
| Potassium Hydroxide | 0.136 | 0.136 | 0.136 | 0.136 |
| TM/UTM Premix | 0.1684 | 0.1684 | 0.1684 | 0.1684 |
| Vitamin A, D, E Premix | 0.0758 | 0.0758 | 0.0758 | 0.0758 |
| Water Sol. Vitamin Premix | 0.0728 | 0.0728 | 0.0728 | 0.0728 |
| Potassium Iodide | 0.00022 | 0.00022 | 0.00022 | 0.00022 |

Examples 13-16

Examples 13-16 illustrate hydrolyzed protein based infant nutritional emulsions of the present disclosure, the ingredients of which are listed in the Table below. All ingredient amounts are listed as kilogram per 1000 kilogram batch of product, unless otherwise specified.

| Ingredient | Example 13 | Example 14 | Example 15 | Example 16 |
|---|---|---|---|---|
| Water | Q.S. | Q.S. | Q.S. | Q.S. |
| Sucrose | 42 | 42 | 42 | 42 |
| Starch | 21.8 | 21.8 | 21.8 | 21.8 |
| Hydrolyzed Protein | 22.2 | 22.2 | 22.2 | 22.2 |
| High Oleic Safflower Oil | 13.7 | 13.7 | 13.7 | 13.7 |
| MCT Oil | 6 | 6 | 6 | 6 |
| Monoglycerol Palmitate | 10 | 9 | 8 | 7 |
| $C_{10}$-$C_{24}$ Fatty Acids | 11 | 9.5 | 8 | 6.5 |
| Coconut Oil | 5 | 7.5 | 9 | 11.5 |
| Fungal Oil | 0.3 | 0.3 | 0.3 | 0.3 |
| Calcium Hydroxide | 1.6 | 1.29 | 1.1 | 0.93 |
| L-Methionine | 0.3 | 0.3 | 0.3 | 0.3 |
| Potassium Phosphate Dibasic | 0.96 | 0.96 | 0.96 | 0.96 |
| Potassium Chloride | 0.3 | 0.3 | 0.3 | 0.3 |
| Ascorbic Acid | 0.235 | 0.235 | 0.235 | 0.235 |
| Carrageenan | 0.0 | 0.0 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Vitamin A, D, E Premix | 0.0758 | 0.0758 | 0.0758 | 0.0758 |
| Water Sol. Vitamin Premix | 0.0728 | 0.0728 | 0.0728 | 0.0728 |
| Potassium Iodide | 0.00022 | 0.00022 | 0.00022 | 0.00022 |

Example 17

In this Example, the absorption and the related bioavailability of $C_{10}$-$C_{24}$ fatty acid calcium salts by rats is evaluated.

Thirty rats are randomly assigned to one of three diets (Diet 1, Diet 2, and Diet 3) containing varying proteins and fats. Diets 1-3 are the same as used in AOAC method 906.48, with the exception that Diets 1-3 have a higher fat level and include maltodextrin as the carbohydrate source. Diet 1 contains 10 wt % protein available as acid casein and 23.6 wt % fat available as an oil blend containing 30 wt % coconut oil, 30 wt % soybean oil, and 40 wt % high oleic safflower oil (HOSO). The nutritional profile of Diets 2 and 3 are identical to the nutritional profile of Diet 1 except that the protein, fat, carbohydrates and minerals are mixed, homogenized and spray dried. Diet 3 differs from Diet 2 only in that the HOSO oil is replaced by calcium high oleic safflower oil fatty acid salts and the tricalcium phosphate is replaced with potassium phosphate such that the overall nutritional and mineral profiles of Diet 2 and Diet 3 are the same. The Ca-HOSO fatty acid salts provide 100% of the dietary calcium.

The rats are fed one of Diet 1, Diet 2, or Diet 3 for a period of 4 weeks. The feed/protein intake and weight gain at the end of the feeding trial are used to calculate feed conversion (gram of weight gain/gram of feed intake) and protein efficiency ratio (gram of weight gain/gram of protein ingested) (PER). If the caloric value (i.e., calories/gram of substance) of the calcium HOSO fatty acid salt is significantly lower than that of HOSO due to poor absorption, then it would be expected that the rats on Diet 3 will either gain less weight or consume more feed to maintain their growth, both of which result in a lower feed conversion and PER.

The results shown in the table below indicate that the rats on Diet 3 have the same feed conversion or PER as the control, indicating that the caloric value of the calcium HOSO fatty acid salt is not different from the HOSO oil. As such, it is shown that the calcium HOSO fatty acid salts are highly bioavailable.

| | Protein Efficiency Ratio | Feed Conversion |
|---|---|---|
| Diet 1 (Control 1) | 2.83 +/− 0.28* | 0.29 +/− 0.03 |
| Diet 2 (Control 2) | 3.16 +/− 0.17 | 0.31 +/− 0.02 |
| Diet 3 (fatty acid calcium salt) | 3.32 +/− 0.27 | 0.37 +/− 0.03 |

*Standard deviation (n = 10)

Example 18

In this Example, the absorption of soy fatty acid salts by 10 day old pigs is analyzed.

Sixteen suckling pigs are randomized into two groups and are individually housed in metabolic cages and trained to take nutritional emulsions from a bowl within 30 minutes. After one week of training on a commercial ready-to-feed hydrolyzed protein based-formula, the pigs are fed either a commercial hydrolyzed protein-based formula powder (Control) including tricalcium phosphate and calcium carbonate as the calcium source, or an emulsion (Experimental Emulsion) including calcium soy fatty acid salts as the calcium source. The protein source and level, fat level and mineral profiles are identical for the Control and Experimental Emulsion. The Experimental Emulsion, however, includes soy fatty acids in place of soybean oil in the Control and includes calcium hydroxide as part of the calcium mineral system to neutralize the soy fatty acids. The potassium phosphate level of the Experimental Emulsion is adjusted to match the phosphorus content of the Control. The calcium soy fatty acids provide 100% of the calcium in the Experimental Emulsion.

Apparent fat and calcium digestibility are calculated based on the following formulas after two weeks of feeding:

Apparent fat digestibility=((fat intake−fecal fat)/fat intake)*100

Apparent calcium digestibility=((calcium intake−fecal calcium)/calcium intake)*100

Dry matter digestibility=((dry matter intake−fecal dry matter)/dry matter intake)*100

A decreased feed conversion (weight/feed intake) and decreased fat, calcium, and dry matter digestibility of the Experimental Emulsion would indicate that the calcium soy fatty acid salts of the Experimental Emulsion are poorly absorbed, and thus, that the caloric value and bioavailability of the calcium are lower for the Experimental Emulsion as compared to the Control.

As shown in the table below, the feed conversion, fat digestibility and dry matter digestibility of the Experimental Emulsion did not differ significantly from the Control indicating that the calcium soy fatty acid salts of the Experimental Emulsion are highly absorbed and bioavailable for neonatal pigs. Further, the apparent calcium digestibility data shown below indicate that the calcium soy fatty acid salts of the Experimental Emulsion are more bioavailable than the calcium included in the Control (i.e., tricalcium phosphate and calcium carbonate).

|  | Apparent fat digestibility | Feed Conversion (Gram of weight gain/ gram of feed (dry matter)) | Apparent calcium digestibility | Apparent dry matter digestibility |
|---|---|---|---|---|
| Control | 97.6 +/− 1.0 | 0.82 +/− 0.14* | 81.8 +/− 7.2 | 97.8 +/− 0.7 |
| Experimental Emulsion | 97.6 +/− 1.4 | 0.80 +/− 0.15 | 91.3 +/− 3.3 | 98.0 +/− 1.0 |

*Standard deviation (n = 10)

Example 19

In this Example, the emulsifying properties of calcium fatty acid salts are analyzed.

A first emulsion (Control Emulsion) is prepared by shearing 18 g of 130° F. soy oil containing monoglycerol palmitate (5% of oil by weight) and 430 mg of Ca (as tricalcium phosphate) with 500 ml of water using a table top high shear mixer. A second emulsion (Calcium Fatty Acid Emulsion) containing an identical level of calcium and fat (12 g of soy oil plus 6 g of soy fatty acids) as the Control Emulsion is prepared by: (1) dispersing soy fatty acid in oil in water at a temperature of about 130° F.; (2) adding 430 mg of Ca as calcium chlorides; (3) adjusting the solution pH to about 7.0 using KOH; and (4) shearing the mixture using a table top high shear mixture.

Figure 1A:
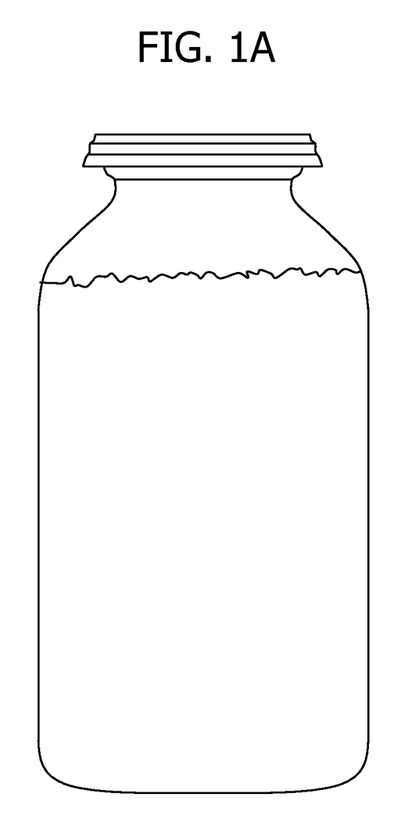
FIGS. 1A and 1B show a drawing of a control emulsion and an experimental emulsion as prepared in Example 19.
Figure 1B:
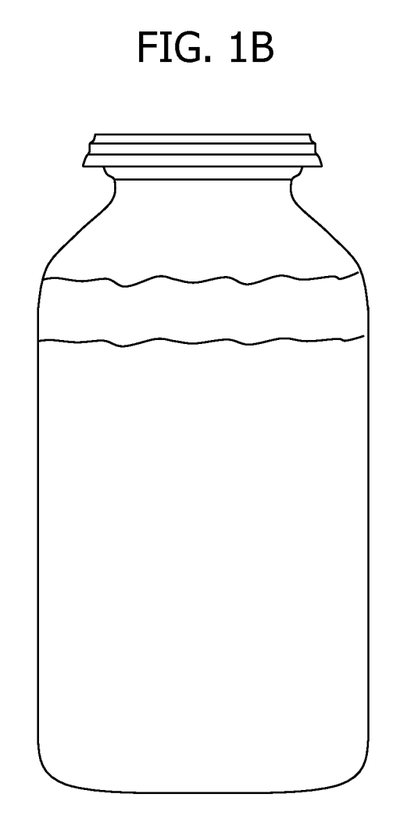

Both the Control Emulsion and the Calcium Fatty Acid Emulsion are allowed to sit for a period of three weeks to analyze emulsion separation. After a single overnight period, the Control Emulsion exhibits a visible phase separation including a creamy layer at the top of the emulsion. (See FIG. 1A). In contrast, after three weeks of storage the Calcium Fatty Acid Emulsion exhibits only a slightly detectable, but not very visible, calcium soap layer on top of the emulsion with the emulsion remaining in one phase. There is no visible calcium sediment at the bottom of the Calcium Fatty Acid Emulsion (See FIG. 1B).

These results indicate that the calcium fatty acid salts are effective emulsifiers and are capable of providing a calcium source to a nutritional emulsion that will not substantially settle out of solution. This allows for an emulsion product with improved stability and longer shelf life.

Example 20

In this Example, the amount of fat absorption and amount of calcium absorption from two separate test formulations and a control formulation in 10 day old pigs is measured.

The first test formulation (Formulation 1) includes palm olein oil in the fat system, the second test formulation (Formulation 2) includes predigested fat in the fat system, and the control formulation (Formulation 3) includes low palmitic acid oil in the fat system. The components of the fat systems of the three formulations are listed in the Table below.

| Nutrient (grams) | Formulation 1 (Palm Olein Oil Formulation) | Formulation 2 (Predigested Fat Formulation) | Formulation 3 (Control Formulation including low palmitic acid oil) |
|---|---|---|---|
| Coconut Oil | 37.2 | 0 | 84.1 |
| High Oleic Safflower Oil | 62.8 | 108 | 111.9 |
| Soy Fatty Acids | 0 | 56.9 | 0 |
| ARA oil | 3.03 | 3.03 | 3.03 |
| DHA oil | 1.52 | 1.52 | 1.52 |
| Monoglycerol Palmitate | 0 | 65.4 | 0 |
| Lecithin | 1.12 | 1.12 | 1.12 |
| Palm Olein | 122.7 | 0 | 0 |
| Soy Oil | 57.1 | 0 | 83.8 |

The three formulations are prepared having nearly identical nutrient and mineral profiles. The fatty acid profile of Formulations 1 and 2 mimic the breast milk fatty acid profile. Calcium hydroxide is included in Formulation 2 (in an amount sufficient to chelate all of the free fatty acids) as a source of calcium, which reacts with the soy fatty acids to form insoluble calcium fatty acid salts. This reaction eliminates the bitterness and throat burning sensation imparted by free fatty acids. In addition, the level of potassium phosphate in Formulation 2 is raised to match the phosphorous level of Formulations 1 and 3. The calcium salt used in Formulations 1 and 3 is calcium phosphate.

Sixty 10 day old pigs (plus or minus two days) are randomized to receive either Formulation 1, Formulation 2, or Formulation 3. Pigs are individually housed in metabolic cages and are fed five times a day for three weeks after four days of training and adaptation. Fecal materials from day two to day eighteen are collected and analyzed for calcium absorption and fat absorption. Calcium absorption is calculated as the amount of calcium in the fecal material divided by the amount of calcium in the diet, multiplied by 100. Fat absorption is calculated as the amount of fat in the fecal material divided by the amount of fat in the diet, multiplied by 100. The results are shown in the Table below.

|  | Fat Absorption (%) | Calcium Absorption (%) |
| --- | --- | --- |
| Formulation 1 (palm olein) | 92.3 ± 3.9 | 88.9 ± 4.7 |
| Formulation 2 (predigested fat) | 98.2 ± 0.7 | 93.1 ± 2.4 |
| Formulation 3 (control: low palmitic acid fat system) | 98.0 ± 1.4 | 90.7 ± 3.5 |

As the results in the above Table indicate, the use of a predigested fat system allows an infant formula to mimic the breast milk fatty acid profile without the adverse effects on calcium and fat absorption as is experienced with a palm olein oil fat system. The fat and calcium absorption rates of Formula 2 (the predigested fat formulation) are at least as good as those of low palmitic acid formula. These findings illustrate that calcium soy fatty acid salts are highly bioavailable in neonatal pigs.

Example 21

In this Example, the postprandial increase in CCK production (AUC) and motilin production (AUC) are evaluated for the pigs of Example 20.

At the conclusion of the fat and calcium absorption analysis described in Example 20, the pigs being administered Formulation 2 (predigested fat formulation) or Formulation 3 (control formulation including low palmitic acid) are fasted for 12 hours, and fasted blood is drawn to isolate plasma. The pigs are allowed two hours to recover and are then given 250 mL of either Formulation 2 or Formulation 3. Postprandial blood samples are drawn at 30 and 60 minutes after feeding and tested for CCK and motilin. The postprandial increase in CCK (area under curve) and motilin (AUC) is calculated. The results are shown in the table below.

|  | Formulation 2 (predigested fat formulation) (pg/mL * min) | Formulation 3 (Control: low palmitic acid formulation) (pg/mL * min) |
| --- | --- | --- |
| Postprandial increase in CCK secretion (area under curve) | 1935 ± 1464 | 1046 ± 754 |
| Motilin AUC (post-prandial increase) | 483 ± 253 | 839 ± 403 |

The data in the table above show that replacing triglycerides with predigested fat (monoglycerol palmitate plus soy fatty acids) stimulates postprandial CCK secretion, which has been shown to stimulate pancreatic digestive enzyme secretion, enhance gallbladder contraction, and retard mouth to cecum transit. As such, formulations with predigested fat may stimulate more digestible enzyme secretion and slow GI transit to allow more nutrient digestion and absorption. Thus, formulations including predigested fat may improve formula tolerance because undigested nutrients can cause excessive colonic fermentation to cause gas, diarrhea, and stomach distension.

In addition, the data in the table above show that replacing triglycerides with predigested fat (monoglycerol palmitate plus soy fatty acids) reduces postprandial motilin secretion. It has been shown that infants with colic have a lower postprandial CCK level but a higher postprandial moltilin level. This imbalance between the postprandial gut hormones causes GI contractions in an infant, which results in abdominal pain. The data in the table above show that the inclusion of predigested fat enhances the postprandial CCK level of an infant but reduces the moltilin level, thus reducing the hormone imbalance to relieve GI contractions, abdominal pain, and colic.

Example 22

In this Example, the pigs of Example 20 are used to study the effect of various fat systems on chylomicron triglyceride palmitic acid and Sn-2 palmitic acid levels.

The 1 hour postprandial blood sample from each pig is drawn and the plasma isolated, frozen by liquid nitrogen, and stored in a freezer at −80° C. Total plasma lipids are extracted using Folch solvent. The triglycerides are isolated by thin layer chromatography. The table below shows the plasma triglyceride palmitic acid and Sn-2 palmitic acid of Formulation 1 (palm olein formulation) and Formulation 2 (predigested fat formulation). The chylomicron triglyceride and Sn-2 palmitic acid of the pigs fed these two formulations are also shown in the table.

|  | Formulation 1: (Palm Olein) | | Plasma triglyceride of pigs fed Formulation 1 | | Formulation 2: (Predigested Fat) | | Plasma triglyceride of pigs fed Formulation 2 | | Plasma triglyceride of breast milk fed human infant | |
| --- | --- | --- | --- | --- | --- | --- | --- | --- | --- | --- |
|  | Tri-glyceride | Sn-2 | Tri-glyceride | Sn-2 | Tri-glyceride | Sn-2 | Tri-glyceride | Sn-2 | Tri-glyceride | Sn-2 |
| Palmitic acid level (%) | 23.3 | 5.8 | 18.3 | 10.6 | 21.4 | 5.2 | 18.5 | 14.4 | 25 | 25.5 |

As shown in the table above, plasma triglyceride from predigested fat formula fed pigs have a significantly higher plasma triglyceride Sn-2 palmitic acid content than the palm olein formula fed pigs. The plasma triglyceride palmitic acid/Sn-2 palmitic acid ratios are about 1.7 and 1.3, respectively, for Formulation 1 and Formulation 2, and it is known that this ratio is about 1.1 for breast fed infants. As such, this data indicates that the predigested fat formulation better mimics breastmilk than does the palm olein fat formulation.

Example 23

In this Example, the pigs of Example 20 are used to study the effect of various fat systems on blood lutein levels.

Plasma from the 1 hour postprandial blood sample from each pig is extracted using a solvent of chloroform and methanol in a 2:1 ratio. The solvent is removed and the resultant lipids are pooled and analyzed for lutein using conventional methods. The table below shows the lutein level of the pigs fed Formulation 1 (palm olein formulation), Formulation 2 (predigested fat formulation), and Formulation 3 (low palmitic acid formulation) in μg of lutein per mg of lipids.

|  | Formulation 1: (Palm Olein) | Formulation 2: (Predigested Fat) | Formulation 3: (Low Palmitic Acid) |
|---|---|---|---|
| Lutein level | N/A* | 0.765 μg | 0.539 μg |

*The lutein level of Formulation 1 is too low to measure.

As shown in the table above, pigs fed formulations including predigested fat have an increased absorption of lutein compared to pigs fed formulations including palm olein or low palmitic acid.

Example 24

In this Example, Formulation 2 (predigested fat formulation) and Formulation 3 (low palmitic acid formulation) of Example 20 are used to study the effects of various fat systems on micelle lutein levels.

Formulation 2 and Formulation 3 are reconstituted with water (133 g of powdered formulation per 1.0 L water), and HCl is added to adjust the pH of the reconstituted formulations to 4.5. The reconstituted formulations are digested for 1 hour at room temperature by adding 1.00 ml of USP pepsin (56 mg/ml) to 40 ml of the reconstituted formulation. The pH of the reconstituted formulations is adjusted to 7.0 after pepsin digestion and then a mixture of 28 mg of USP pancreatin amylast/protease, 28 mg of USP pancreatin lipase, and 108 mg of bile extract is added to the pepsin digested formulations. The formulations are further digested at room temperature for 2 hours and centrifuged (31,000 g at 20° C. for 3 hours). The digested formulations form an oil/cream plug, an aqueous phase, and a sediment layer. The aqueous phase is withdrawn for lutein analysis of micelles, which act as carriers during the absorption of lutein in the aqueous lumen. The table below shows the level of micelle lutein per kg of digested formulation.

|  | Digested Formulation 2: (Predigested Fat) | Digested Formulation 3: (Low Palmitic Acid) |
|---|---|---|
| Micelle Lutein (μg) | 0.598 μg | 0.246 μg |

As shown in the table above, the amount of micelle lutein found in the digested formulation including predigested fat was more than twice the amount of micelle lutein found in the digested formulation including low palmitic acid, thus indicating that the use of predigested fat can increase lutein absorption.

Example 25

In this Example, the ability of predigested fat to reduce the incidence of loose stool is analyzed.

Thirty weaned rats are fed a hydrolyzed protein based powder infant formula, comprising MCT oil as 30 wt % of the fat source for an adaptation period of four days. At the end of the adaptation period, the rats are randomly assigned to two groups and fed either a Control Formulation (low palmitic acid powder infant formula) or a Test Formulation (predigested fat containing infant formula). The nutrient profile of the Control Formulation and the Test Formulation are identical. The rats are allowed free access to feed and water for a period of five days, and the amount of feed ingested and body weight are recorded daily.

Figure 2:
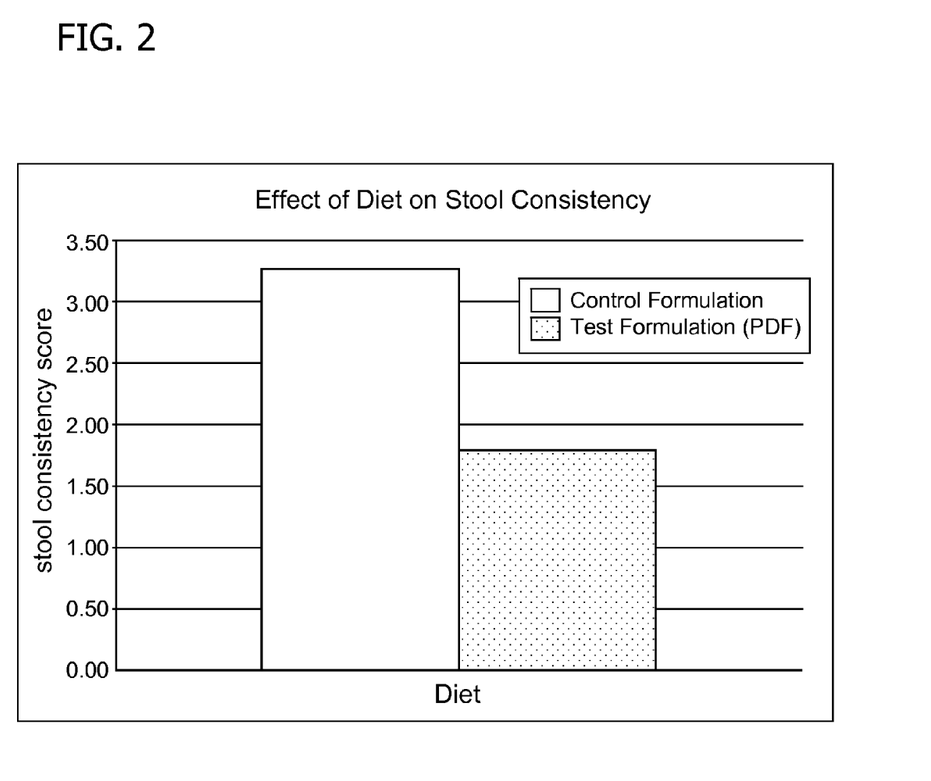
FIG. 2 is a chart showing the effect of diet on stool consistency.

Although there is no significant difference in feed intake or weight gain between the two groups, there is a significant difference in stool consistency. The stool consistency of the rats is scored using a 0-5 point system during the last two days of feeding. Scoring is based on the severity and the consistency of the stool sticking to a blotting sheet at the bottom of the cage. A score of 0 indicates normal stool and a score of 5 indicates watery diarrhea. As shown in FIG. 2, the rats fed the Control Formulation (containing the MCT oil) produced looser stools than the rats fed the Test Formulation (containing the predigested fat).

Example 26

In this Example, the ability of predigested fat to reduce the incidence of necrotizing enterocolitis (NEC) is analyzed.

Pre-term pigs (92% gestation) delivered via cesarean section are immediately transferred to an oxygenated incubator (37° C.), and a vascular catheter is placed in an umbilical artery. The pigs are given three injections (4, 6, and 7 mL/kg body weight) of maternal plasma via the vascular catheter during the first 24 hours. Total paternal nutrition (TPN) is provided at a rate of 4-6 mL/kg/hour for 24 hours. The pigs are then randomized to receive either a Control Formulation or a PDF Formulation at a rate of 5 mL/kg/hour via an orogastric tube. The Control Formulation and the PDF Formulation are identical with the exception of the fat systems therein. Specifically, the fat system in the Control Formulation includes vegetable oil, and the fat system in the PDF Formulation includes 30 wt % monoglycerol palmitate, 20 wt % soy fatty acids, 26 wt % high oleic safflower oil, 14 wt % coconut oil, and 10 wt % tributyrin. Both the Control Formulation and the PDF Formulation include 100 g protein, 47 g fat, and 50 g corn syrup per liter of formulation. The pigs are euthanized after 36 hours of enteral feeding and necropsy is conducted to assess the severity of the NEC lesions using a scoring system of 1-5 with a score of 1 indicating no signs of NEC. The results are shown in the table below.

|  | Block 1 | | Block 2 | |
| --- | --- | --- | --- | --- |
|  | Control Formulation (n = 5) | PDF Formulation (n = 3) | Control Formulation (n = 5) | PDF Formulation (n = 3) |
| Early NEC death | 2 | 0 | 3 | 1 |
| NEC detected at necropsy | 2 | 1 | 0 | 0 |
| Total NEC | 4 | 1 | 3 | 1 |

As shown in the table above, five of the ten pigs (50%) being fed the Control Formulation die of NEC before the conclusion of the enteral feeding period, but only one of the six pigs (16.7%) fed the PDF Formulation die of NEC before the conclusion of the enteral feeding period. In addition, seven of the ten pigs (70%) being fed the Control Formulation were determined to have NEC at the conclusion of the enteral feeding period, while only two of the six pigs (33%) being fed the PDF Formulation were determined to have NEC at the conclusion of the enteral feeding period. Thus, it can be concluded that by replacing a fat system of vegetable oil with a fat system including predigested fat, the incidence of NEC can be decreased.

What is claimed is:

1. A method for improving tolerance of an infant, toddler, or child, the method comprising administering to the infant, toddler or child a nutritional product comprising at least 0.2 wt % of total dry matter of at least one of a free fatty acid component and fatty acid-containing monoglycerides, wherein at least 70% of the fatty acids in the fatty acid-containing monoglycerides are at the Sn-1 position.

2. The method of claim 1, wherein the fatty acid-containing monoglycerides are monoglycerol palmitate.

3. The method of claim 1, wherein the free fatty acid component is in a form selected from the group consisting of calcium fatty acid salts, magnesium fatty acid salts, and combinations thereof.

4. The method of claim 1, wherein the free fatty acid component comprises less than 15 wt % saturated fatty acids with a chain length of longer than 14 carbon atoms.

5. The method of claim 1, wherein the free fatty acid component is derived from a vegetable oil.

6. The method of claim 5, wherein the vegetable oil is selected from the group consisting of olive oil, canola oil, corn oil, soybean oil, and combinations thereof.

7. The method of claim 6, wherein the vegetable oil is soybean oil.

8. The method of claim 1, wherein the free fatty acid component is derived from fractionated animal fat having less than 20% (by weight) total myristic acid, palmitic acid, and stearic acid.

9. The method of claim 8, wherein the free fatty acid component is derived from fractionated animal fat having less than 2% (by weight) total myristic acid, palmitic acid, and stearic acid.

10. The method of claim 5, wherein the vegetable oil comprises less than 20% (by weight) total myristic acid, palmitic acid, and stearic acid.

11. The method of claim 1, wherein the fatty acid-containing monoglycerides are derived by enzymatic hydrolysis of lard, tallow, or combinations thereof.

12. The method of claim 1, wherein the nutritional product is free of carrageenan.

13. A method for improving digestion in an infant, toddler, or child, the method comprising administering to the infant, toddler or child a nutritional product comprising at least 0.2 wt % of total dry matter of at least one of a free fatty acid component and fatty acid-containing monoglycerides, wherein at least 70% of the fatty acids in the fatty acid-containing monoglycerides are at the Sn-1 position.

14. The method of claim 13, wherein the fatty acid-containing monoglycerides are monoglycerol palmitate.

15. The method of claim 13, wherein the free fatty acid component is in a form selected from the group consisting of calcium fatty acid salts, magnesium fatty acid salts, and combinations thereof.

16. The method of claim 13, wherein the free fatty acid component comprises less than 15 wt % saturated fatty acids with a chain length of longer than 14 carbon atoms.

17. The method of claim 13, wherein the free fatty acid component is derived from a vegetable oil.

18. The method of claim 17, wherein the vegetable oil is selected from the group consisting of olive oil, canola oil, corn oil, soybean oil, and combinations thereof.

19. The method of claim 18, wherein the vegetable oil is soybean oil.

* * * * *